United States Patent [19]

Wiczer

[11] 4,305,933

[45] Dec. 15, 1981

[54] THICKENED GELATINOUS EDIBLE ALCOHOLIC MEDICATED CARRIER

[76] Inventor: Sol B. Wiczer, 1600 S. Eads St., Apt. 224N, Arlington, Va. 22202

[21] Appl. No.: 129,100

[22] Filed: Mar. 10, 1980

[51] Int. Cl.³ ............................................ A01N 31/00
[52] U.S. Cl. .................................... 424/180; 424/34; 424/35; 424/360; 424/361; 424/362
[58] Field of Search ................... 424/34, 35, 180, 361, 424/360, 362

[56] References Cited

U.S. PATENT DOCUMENTS

| | | | |
|---|---|---|---|
| 57,561 | 8/1866 | Petre | 424/180 |
| 75,536 | 3/1868 | Detmars | 424/180 |
| 115,698 | 6/1871 | Burroughs | 424/361 |
| 219,957 | 9/1879 | Kampman | 424/195 |
| 234,785 | 11/1880 | King | 424/195 |
| 239,564 | 3/1881 | Smith | 424/195 |
| 2,530,480 | 11/1950 | Pitkin | 424/35 |
| 3,085,942 | 4/1963 | Magid et al. | 424/360 |
| 3,133,863 | 5/1964 | Tansey | 424/35 |
| 3,134,720 | 5/1964 | Green et al. | 424/362 |

FOREIGN PATENT DOCUMENTS

| | | | |
|---|---|---|---|
| 326447 | 3/1930 | United Kingdom | 424/361 |
| 1082624 | 9/1967 | United Kingdom | . |

OTHER PUBLICATIONS

Remington's Pharmaceutical Sciences 15th Ed., (1975), pp. 356, 357, 752, 803–804, 1008, 1228, 1240, 1241–1243, 1252–1253, 1256, 1448 & 1578–1579.

Primary Examiner—Stanley J. Friedman

[57] ABSTRACT

Beverage alcoholic liquid is mixed as a carrier with compatible medicating substances to be taken orally, and the mixture is thickened to a heavy fluid or solid gel by addition of an edible gelating agent such as gelatin, low methoxyl pectin, alkali pectate, carboxy methyl cellulose and methyl cellulose.

11 Claims, No Drawings

THICKENED GELATINOUS EDIBLE ALCOHOLIC MEDICATED CARRIER

This invention relates to a normal beverage alcohol liquid thickened to viscous fluid up to solid gelatinous form, useful as a desirable tasteful beverage product which may be sipped as a thick syrupy liquid or eaten as a solid gel and which is filled with useful medicating agents as a carrier therefor of the character of liquid medicinal extracts, cough medicant mixture, tonics, vitamins or solid medicant substances such as aspirin, antibiotics, antacids, laxatives or other edible alcohol-compatible medicating solids or liquids.

According to the present invention an alcoholic product, typically liqueurs, brandies, whiskeys or gins are thickened to heavy viscous thickened liquids up to gelatinous solids, by adding an edible thickening agent to the normally low viscosity beverage to which the medicating agent is to be added, or the preformed mixture or blend of beverage and medicating agent has the thickening agent added, in quantity to provide a thick syrupy liquid up to a gelatinous solid alcoholic beverage product using an alcohol gelating agent.

The thickening-gelating agent is a member of the group consisting of gelatin, low methoxy pectin, alkali pectate, carboxy methyl cellulose (CMC) and methyl cellulose. Mixtures of these gelating substances may also be used. The preferred pectin hereof is a hydrolized or low methoxy pectin having most of the methoxyl groups removed, such as less than 10% methoxyl groups in the pectin. Such low methoxyl pectins are further described in U.S. Pat. Nos. 2,132,065, 3,982,003 and 3,973,051.

These patents teach low methoxyl pectins and their preparation as gelating agents for generally aqueous food compositions. For instance, in numerous examples U.S. Pat. No. 3,973,051 shows the preparation of low methoxyl pectin from crude natural pectin sources, such as citrus fruits, and define the product as having generally less than 2% of methoxyl groups, listing in examples specifically a composition of pectin having 1% of methoxyl groups (example 1), 10% methoxyl in example 16, and pectin having no methoxyl group in example 2, all forming good gels for a food product, the disclosure and examples of these patents being here included by reference.

In practicing the invention the alcoholic beverage generally having an alcohol content of at least 25 proof and possibly ranging as high as 150 proof, more usually 50 to 120 proof, selected from liqueurs, cordials, brandies, rums, whiskeys, gins or the like of selected taste is used as the base beverage. It is used as a carrier gel for one or more medicating substances so that the medicant or mixture may first be added to the light liquid beverage and dissolved or suspended therein with agitation for even distribution in the beverage liquid. The medicating substances may also be added by mixing into the thickened or gelated form of the beverage alcohol. The latter is less desirable since the gel form may be less stable when agitated in such addition.

Such medicating substances are those commonly known and used in the medicating art, typically liquid or solid medicating substances to which the beverage will impart a desired taste as a carrier. Therefore the medicating agent will be blended with the beverage in quantity to provide the medication in small reasonable dosages of a teaspoonful to an ounce or two of the alcoholic blend or to a desired medicating dosage, variable with the particular medicating substance as normally would be prescribed. The beverage with or without medicine first added, has added thereto the gelating agent or mixture of gelating agents in quantity useful to provide the desired thickening or solidifying effect. The quantity will generally range from 0.2–3% of gelating agent, based upon the alcoholic beverage or blend thereof with the medicating agent, where the beverage is merely to be thickened or bodied as a viscous liquid, up to 10% preferably 4–8%, where the beverage liquid is to be thickened to a substantially solid gelatinous body.

The gelating agents listed have various desirable characteristics each of their own and may be selected for their advantages as individual or mixtures. The gelatin imparts less taste, but has a significant calorific value. It can form firm gels cold when admixed with the methyl cellulose or low methoxyl pectin, but the gel also forms by warming slightly in a mixture with the liquid beverage, heating to a range of 100°–140° F., preferably about 115°–125° F., variable in this range with the stability and volatility of the medicating agent. Where the latter is quite volatile, it would be preferred first to add the gelatin in quantity to form the gel and then, upon cooling and before setting, to add the medicating substance with mixing. Where the beverage base mixed with the medicating agent is a clear liquid, the gelatin will convert the product to a clear gel or thicken it only to a thick liquid.

The pectin is a low methoxyl pectin and will form a gelatinous liquid by mixing in the cold in low quantities up to 3%, but higher quantities such as 3 to 6% by weight forms solid gels.

The methyl cellulose and carboxy methyl cellulose are superior to either in forming a firmer gel without significant syneresis, and easily by mere mixing in the cold. The methyl cellulose or carboxy methyl cellulose have no food value, but are merely inert, in contrast to the other gelating agents. Their gels formed cold have higher stability which makes these gelating agents preferably used as a mixture with the low methoxyl pectin to reduce the syneresis, or with gelatin to provide more stability.

Thus, the products hereof will range from thickened liquids to solid gels using an improved alcoholic beverage as a taste and flavor imparting base carrier for medicinal substances as stated. As a carrier for medicinal products, and particularly for one often having a taste imparting alcoholic beverage advantage, these gelating thickening agents appear also to add a useful soothing non-irritating effect upon the gastro-intestinal tract, as well overall to impart a slight sedative and tranquilizing effect, in which the components are either easily digested or are inert, except for the common medicating function of the added medicant substance.

EXAMPLE 1

200 cc of a strong 100 proof rum is mixed cold with 2 grams (1% by weight) of 4000 cps methyl cellulose, and the rum becomes immediately thickened to a heavy syrupy condition barely fluid, as a thick molasses. It is blended with 100 cc of a commercial cough syrup comprising 0.5% by weight of methapyralene and 0.5% by weight of d-methorphan dissolved in a sugar syrup and used as a cough syrup. The same product may be modified by reducing the content of sugar solution to selected taste of the user. The quantity of gelating agent may be increased to 4 grams and the product then will immediately thicken to a solid gel and may be taken in spoonful lots as a gelatinous medicating substance useful as a cough medicine. A similar product may be made lowering the alcoholic strength of the beverage base to any desired, from about 25–90 proof, according to selected taste. Selected properties of the cough medicine such as to impart a decongestant or body pain reducing effect by further addition of such common medicating substances as triaminic, aspirin or the like.

EXAMPLE 2

100 cc of 90 proof Cointreau liqueur, a commercial cordial, is mixed with 6 grams of powdered gelatin and then heated as a slurry for 4 or 5 minutes to 120° F. Powdered aspirin (sodium acetyl salicylate), in quantity of 6½ grams, is stirred into the warmed liquid and is then allowed to cool. The solution upon standing cold for about an hour will set to a solid gelatinous mass, whereby approximately 1 spoonful (5 grams) will contain about a normal dosage of aspirin, and the quantity can be varied as desired. In a similar manner the same alcohol based liquid having the gelatin dissolved therein and before setting at ambient temperatures, can have added thereto other typical solid orally-taken medicating substances, that can be dissolved or suspended in the alcohol base liquid as desired, such as individual vitamins or vitamin mixtures, antacids, such as magnesium hydroxide or aluminum hydroxide, or powdered mixtures with each other, or with other medicating substances to be taken orally, cinepidene, organic extracts, glyceryl guiacolate, high-alcohol elixirs or the like. Moreover, it may be preferred to distribute an alcohol insoluble substance in the form of small tablets of measured quantity such as ⅛ to ¼ gram size, distributed as a suspension of numerous tablets in the gel body, so that a spoonful dose of gel may have one or two tablets suspended in the gel when taken orally.

EXAMPLE 3

100 cc of a commercial 80 proof bourbon whiskey has mixed therein 4 grams of low methoxyl pectin, having less than 2% of methoxyl groups, evenly distributed by stirring in the cold, whereby the beverage is converted to a thick syrupy liquid of about 40 cps at 20° C. The product is further mixed with 0.5 grams methapyralene and 0.5 grams of d-methorphan to form thereof a thick syrupy cough liquid containing these common cough medicating components, but essentially free of sugar or other flavoring agents. The product may be further thickened to gelate to a solid gel by the further addition of 2 grams of methyl cellulose, as in example 1. Alternatively, the product is further modified by adding with mixing an additional 3 grams of the same less than 2% low methoxyl pectin.

EXAMPLE 4

The example 3 is repeated except that 5 grams of carboxy methyl cellulose (Hercules CMC) is mixed with 100 cc of Napoleon Brandy containing the same medicating components as a solution, the brandy being of 80 proof, the mixing being applied cold in the cold, and sets by stirring for 2 minutes to a solid gel.

For this same alcohol base carrier, other medicating substances may be substituted as stated above, in normal dosage quantity, whereby the typical dosage of the alcohol beverage product base hereof, in moderation, such as one of two teaspoonful doses will form a useful dosage of both the carrier base and medicating substance.

As thus described, orally useful medicating substances are disposed in a beverage alcohol base in concentration to form a useful dosage of both the alcohol beverage and medicating substance.

I claim:

1. In an oral medicating product having an alcohol containing base containing orally ingestible medicating substances compatibly ingestible in the said alcohol containing base, the improvement comprising
    a taste imparting beverage alcohol having an alcoholic proof strength in the range of about 25–120 as said alcoholic base,
    medicating substances homogeneously distributed in said beverage alcohol base in concentration to provide a medicating effect in small unit dosage quantities of said medicating product, said product being,
    gelated with about 3–10% of a gelating agent selected from the group consisting of gelatin, low methoxyl pectin and alkali pectate to provide a substantially solid medicating gel.

2. The product of claim 1, wherein the pectin is a low methoxyl pectin having less than 10% methoxy groups.

3. The product of claim 1, wherein the gelating substance is gelatin.

4. The product of claim 1, wherein the gelating gent is a mixture of gelating agents in said quantity range of low methoxyl pectin having less than 10% methoxyl groups in quantity of about 3 to 7%, and the remainder, at least about 2% methyl cellulose.

5. The product of claim 1, wherein the medicating substance is a member of the group consisting of high alcohol elixirs, vitamins, organic extracts, cough medicines, pain relievers, medicants, antacids, laxatives, compatibly ingested in an alcohol base as an oral medicant in concentration to be taken orally in small dosage quantities.

6. The product of claim 1, wherein the medicating substance is a cough syrup compatibly ingested with said beverage to use in small dosage quantities.

7. The product of claim 1, wherein said beverage alcohol base is a member of the group consisting of liqueurs, cordials, brandies, rums, whiskeys and gins.

8. In a process of forming an oral medicating product having an alcohol containing base and containing orally ingestible medicating substances, the improvement comprising the steps of
    adding said medicating substance to a strong taste imparting beverage alcohol in the range of 25–120 proof,
    adding as said medicating substance one which is compatibly ingestible with said strong beverage alcohol base in concentration therein to provide a medicating effect in small unit dosage quantities of said medicinal product, and
    adding to said alcohol composition about 3–10% of a gelating agent selected from the group consisting of gelatin, low methoxyl pectin having less than 10% methoxyl groups and alkali pectate and mixing the alcoholic medicinal product at raised temperature above about 100° F. with stirring to dissolve said gelating agent and then cooling to set to a substantially solid medicating gel.

9. The method as defined in claim 8, wherein the gelating agent is gelatin.

10. The method as defined in claim 8, wherein the gelating agent is low methoxyl pectin having less than 10% methoxyl groups and the mixture is heated to a temperature in the range of 100°–140° F. with stirring to dissolve the pectin and then by cooling to set to a substantially solid medicating gel.

11. The method as defined in claim 8, wherein the gelating agent is alkali pectate and the mixture is heated to a temperature in the range of 100°–140° F. with stirring to dissolve the pectin and then by cooling to set to a substantially solid medicating gel.

* * * * *